(12) United States Patent
Day et al.

(10) Patent No.: US 9,861,405 B2
(45) Date of Patent: Jan. 9, 2018

(54) POLYAXIAL LOCKING ASSEMBLY

(71) Applicant: ORTHO SOLUTIONS LIMITED, Essex (GB)

(72) Inventors: Adrian Day, Surrey (GB); Kevin Stamp, Sheffield (GB)

(73) Assignee: Ortho Solutions UK Limited, Essex (GB)

( * ) Notice: Subject to any disclaimer, the term of this patent is extended or adjusted under 35 U.S.C. 154(b) by 410 days.

(21) Appl. No.: 14/398,809

(22) PCT Filed: May 8, 2013

(86) PCT No.: PCT/GB2013/051198
§ 371 (c)(1),
(2) Date: Nov. 4, 2014

(87) PCT Pub. No.: WO2013/167895
PCT Pub. Date: Nov. 14, 2013

(65) Prior Publication Data
US 2015/0112395 A1    Apr. 23, 2015

(30) Foreign Application Priority Data
May 8, 2012   (GB) .................................. 1207975.2

(51) Int. Cl.
*A61B 17/80* (2006.01)
*A61B 17/17* (2006.01)

(52) U.S. Cl.
CPC ...... *A61B 17/8038* (2013.01); *A61B 17/8047* (2013.01); *A61B 17/8066* (2013.01); *A61B 17/1728* (2013.01)

(58) Field of Classification Search
CPC ............ A61B 17/8047; A61B 17/8033; A61B 17/8038; A61B 17/8066; A61B 17/8061
USPC .................................................. 606/287–290
See application file for complete search history.

(56) References Cited

U.S. PATENT DOCUMENTS

| | | | | |
|---|---|---|---|---|
| 2005/0004574 A1* | 1/2005 | Muckter | ............ | A61B 17/8047 606/280 |
| 2005/0049593 A1* | 3/2005 | Duong | ............... | A61B 17/8047 606/287 |
| 2005/0049595 A1* | 3/2005 | Suh | ..................... | A61B 17/7059 606/71 |
| 2005/0228386 A1* | 10/2005 | Ziolo | ................ | A61B 17/8047 606/86 B |
| 2006/0100626 A1* | 5/2006 | Rathbun | ............ | A61B 17/1728 606/86 B |
| 2006/0235403 A1* | 10/2006 | Blain | ................. | A61B 17/7059 606/249 |
| 2006/0241618 A1* | 10/2006 | Gasser | ............... | A61B 17/8047 606/287 |
| 2007/0118125 A1* | 5/2007 | Orbay | ................. | A61B 17/8047 606/279 |
| 2007/0233116 A1* | 10/2007 | Olerud | ............... | A61B 17/8047 606/86 A |
| 2009/0088807 A1* | 4/2009 | Castaneda | .......... | A61B 17/8047 606/286 |

(Continued)

*Primary Examiner* — Matthew Lawson
*Assistant Examiner* — Amy Sipp
(74) *Attorney, Agent, or Firm* — Maine Cernota & Rardin

(57) ABSTRACT

A locking mechanism for a polyaxial locking screw is provided, together with a polyaxial locking assembly for locking a receiving member to a substrate. Also provided is a plating system for pelvic reconstruction.

1 Claim, 10 Drawing Sheets

(56) References Cited

U.S. PATENT DOCUMENTS

2011/0238122 A1* 9/2011 Gradl ................. A61B 17/8052
　　　　　　　　　　　　　　　　　　　　　606/289
2013/0190825 A1* 7/2013 Perrow .............. A61B 17/8042
　　　　　　　　　　　　　　　　　　　　　606/281

* cited by examiner

POLYAXIAL LOCKING ASSEMBLY

RELATED APPLICATIONS

This application is a national phase application filed under 35 USC §371 of PCT Application No. PCT/GB2013/051198 with an International filing date of May 8, 2013, which claims priority to GB 1207975.2, filed May 8, 2012. Each of these applications is herein incorporated by reference in their entirety for all purposes.

The present invention relates to a locking mechanism for use with a receiving member, such as a plate. More particularly, the present invention relates to a locking assembly for locking a receiving member to a substrate by means of at least one screw which can be passed through at least one cavity in the receiving member and can be fixed into the substrate. The locking assembly is polyaxial, such that the system allows the at least one screw a range of motion along several different axes relative to the receiving member. This permits the screw to extend into the substrate in a desirable orientation.

Numerous receiving members are known in the art, and include any member which would be desired to fix to a substrate. For example, the receiving member may be a bracket; and the substrate a wall, or the receiving member may be a plate; and the substrate a bone. The present invention has various applications in construction, such as in furniture, fixtures and fittings; or in human or animal medicine, such as in the fixation of implants, plates, rods and other such devices.

The use of a polyaxial locking assemblies is advantageous, for example where the hole (which can be predrilled into the substrate prior to insertion of the screw) is at an angle to the cavity in the receiving member, or if the substrate itself is not uniform and it is not possible to align the axis of the cavity and the part of the substrate suitable for screw insertion. Polyaxial locking systems can also have an advantage in that screws inserted at diverging angles may provide a stronger fixation of the receiving member to the substrate.

Polyaxial locking systems are known in the art, but the invention provides an alternative improved version.

Accordingly the invention provides a polyaxial locking assembly comprising;

A bushing with a partially spherical outer surface sized and shaped to closely conform with a cavity in a receiving member, characterised in that the bushing further comprises a groove around a circumference of the bushing, said groove being shaped so that the bushing, at that circumference, provides a cam having at least one lobe; there is further provided an anti-rotation member having a substantially annular geometry and a radial thickness R and being contoured such that at least one portion (R2/511) of the anti-rotation member has an effective radial thickness R2 greater than that of at least one other portion R1 such that in use, rotation of the bushing around an axis (521) perpendicular to the plane of the groove (522) causes the at least one lobe of the cam to engage with the at least one effectively radially thicker portion of the anti-rotation member, forcing the anti-rotation member to engage with the cavity so as to lock the assembly in a desired orientation.

Preferentially, the cavity is provided with at least one radially outwardly protruding keyway and the anti-rotation member is provided with a key for cooperative engagement with the keyway such that rotational motion of the anti-rotation member within the cavity is restrained. In a further preferential embodiment, the cavity is of partially spherical cross-section.

In a further preferential embodiment, the assembly is further provided with a screw. The bushing is preferentially provided with a hole for the insertion of such a screw or bolt or other item such as a drill bit. The hole in the bushing is preferentially such that it has an axis or centreline perpendicular to the plane of the groove in the bushing, which is also the plane in which the bushing has a cross-section in the form of a cam profile. The cam profile has at least one lobe but may have further such lobes. In the preferential embodiment shown in the attached Figures, the cam profile has four such lobes. Where a screw and a hole are provided, a means of engagement between them is preferable. In the embodiment shown in FIG. 9 and particularly FIG. 18, the hole is provided with a female threading and the screw is provided with an engagement section 517 provided with a male threading. The engagement section is shown as tapered although any means of providing a stop beyond which the screw cannot pass any further through the bushing will mean that further rotation of the screw will result in rotation of the bushing and the engagement of the locking mechanism. Any of the components, the bushing, the anti-rotation member, the inner wall of the cavity, or the screw, can be provided with a high-friction surface to facilitate the action of the locking mechanism. It will be obvious to those skilled in the art that the eventual locked position of the bushing and/or screw within the assembly, once locked, enables the axis of the screw and/or bushing to be in any one of a wide range of orientations, as the skilled person would expect of a polyaxial locking mechanism.

In another aspect of the invention, an anti-rotation member for use in a polyaxial locking assembly, having a substantially annular geometry and a radial thickness R and being contoured such that at least one portion of the anti-rotation member has an effective radial thickness R2 greater than that of at least one other portion R1, is provided. The member may have a closed or open circumferential geometry and so may be generally ring-shaped or c-shaped.

In a preferential embodiment, the anti-rotation member is provided with a key for engagement with a keyway in a cavity.

In another aspect of the invention, there is provided a bushing for use in a polyaxial locking system having a contoured section in at least one plane having a cross section with a cam profile, said cam profile having at least one lobe, as seen in FIG. 15. In the Figure the cam profile of a preferential embodiment is shown as a shaded, cross-sectionalised area.

Preferentially the outside profile of the bushing is substantially spherical where it is not truncated by holes passing through it or the groove/cam profile section. This allows for the polyaxial motion of the bushing within a cavity of a receiving member. It will be recognised that a generally spherical bushing will provide polyaxiality in a cavity that is not itself spherical, for example a simple tube, and a non-generally spherical bushing will allow for polyaxiality if it is within a cavity that is generally spherical in cross-section.

Preferably the bushing is provided with a hole having an axis perpendicular to the plane of the contoured section. The contoured section is that section defined by the groove which has a cam profile in cross-section. The hole may be blind or a through hole and may be provided with a rough surface or may be provided with a threading for engagement with a screw as otherwise herein described. The hole may be tapered to cooperate with a tapered section of a screw or bolt.

In another aspect of the invention, there is provided a polyaxial locking assembly comprising; a receiving member comprising at least one open cavity having a generally spherical inner surface; a bushing with a generally spherical outer surface sized and shaped to fit within the cavity, said bushing comprising a hole aligned with an axis of the bushing, said hole further provided with a female thread; a screw provided with a male thread for engagement, in use, with the bushing and the hole and thread thereof; characterised in that the open cavity is provided with at least one radially outwardly protruding keyway; the bushing further comprises a groove aligned with a circumference of the bushing, said circumference being on a plane substantially orthogonal to the bushing axis, the bushing groove being shaped so that the bushing, at that circumference and on that plane, provides a cam, said cam having at least one lobe; there is further provided an anti-rotation member that, in use, locates in the bushing groove between the cam geometry and the inner surface of the cavity, the anti-rotation member further comprising a key for cooperative engagement with the cavity keyway such that the ability of the anti-rotation member to rotate within the cavity is restrained; the anti-rotation member further having a generally annular, open or closed geometry and having a radial thickness R, and further being contoured such that at least one portion 511 of the anti-rotation member has an effective radial thickness R2 greater than that of at least one other portion R1; such that in use, the screw may be threaded into the bushing until it reaches a limit of travel, whereupon further rotation of the screw also rotates the bushing and the at least one lobe of the cam translates rotationally so as to engage with the at least one effectively radially thicker portion of the anti-rotation member, forcing the effectively radially thicker portion of the anti-rotation member outwards so that the anti-rotation member engages with the inner surface of the cavity and causes a build up of friction between the cam, the anti-rotation member and the inner surface of the cavity, so as to lock the assembly in a desired orientation.

Locking mechanisms are used in various applications in the prior art, most notably with plates for affixing to bones of the human or animal body. Whilst the present invention is not so limited, one possible use of the locking system is in plates for affixing to bones. In particular, the locking mechanisms can be used in plates for the reconstruction of the pelvis.

Pelvic reconstruction may be required following trauma that results in significant fractures to the bone structure of the pelvis. Such trauma typically arises in motor vehicle or cycling accidents or falls from a significant height. Severe trauma can result in the complete disruption of the sacroiliac complex leading to both rotational and vertical instability.

Pelvic reconstruction is challenging as a result of the large number of internal organs cradled by the pelvis and the associated considerable blood flow in the region. Despite the complex environment in which such surgery is carried out, the plates used to date are basic in comparison with some of the more advanced areas of reconstructive surgery, for example the reconstruction of long bones.

The present invention has arisen in order to address the problems associated with current technologies.

According to a further aspect of the present invention there is provided a locking mechanism for a polyaxial locking screw, the mechanism comprising: a plate comprising at least one opening that is provided with a female thread; a bushing provided with a male thread sized to interface with the female thread of the plate; and a split grommet with a female thread for engagement, in use, with the polyaxial locking screw.

The opening in the plate may have a spherical cross-section. The plate has an upper surface through which the screw enters in use and lower surface from which the screw emerges in use, and wherein the lower surface is scalloped to ensure the grommet does not contact the bone and also to maximise the blood supply to the bone through the soft tissue.

The bushing may have a radially inwardly protruding tab to limit the rotation the grommet. The tab may constrain rotation of grommet to 8°, which is 4° to either side of the neutral position. The inner surface of the bushing may have a spherical cross-section.

The external surface of the grommet may have a spherical cross-section. The threads on the plate and/or the bushing and/or the grommet may have a square section in order to resist cross-threading.

The locking mechanism may further comprise at least one locking screw. The locking screw may be provided with a locking mechanism engagement thread for engagement with the female thread of grommet. The portion of the screw comprising the locking mechanism engagement thread may be tapered or conical in shape to cause radial expansion of grommet as the screw is engaged or introduced. A bone engagement thread may be provided in a distal portion of the screw. The bone engagement thread may be self drilling, self-tapping and reverse cutting. The bone engagement thread may be cortical or it may be cancellous.

Furthermore, according to the present invention there is provided a plating system for the anterior pelvic ring, the system comprising at least two locking mechanisms as described above, wherein the plate is common to the at least two locking mechanisms.

The openings may be configured to lie in the same plane. The configuration of the openings within the plane may be arcuate. The plate may be wasted around each opening. The plate may be tapered at its ends in order to facilitate the plate being provided beneath the soft tissues in a minimally intrusive procedure.

Furthermore, according to the present invention there is provided a plating system for the posterior pelvic ring, the system comprising at least four locking mechanisms as described above, wherein two locking mechanisms are provided on each of two mirror image plates.

Each plate may have three, four or five locking mechanisms. The plating system may further comprise at least one transverse rod configured to join together the two plates using one locking mechanism in each plate. Alternatively, the plating system may comprise two transverse rods, each configured to join together the two plates. The two transverse rods may be substantially parallel, thereby creating a trapezoid in conjunction with the two plates. The system may further comprise a grub screw for aiding the attachment of each transverse rod to each plate.

In a configuration in which each plate has at least three locking mechanisms, a three point fixation system is provided which provides poly-axial fixation in three-dimensional space. The polyaxial nature of the plating system ensures that the locking mechanisms are configured to provide polyaxial support whilst not being solely reliant on the thread to avoid pull-out. Instead, the interface between the plurality of locking mechanisms and the plate provides a unique three dimensional fixation which is both stable and robust. The innovation of the contoured plate provides a considerable advantage over known triangular osteosynthesis techniques as the plate anchors the locking mechanisms providing additional stability to the system.

The plate may be contoured to conform to the shape of the pelvis by providing an angular deviation between adjacent openings between 0° and 65°. The angular deviation between adjacent openings may be simultaneously in more than one plane. The plating system may further comprise a hook assembly for attaching a spinal instrumentation system to one of the transverse rods. The hook assembly may comprise a rod holder, an aperture restriction ring and a grub screw. The rod holder may have a substantially C-shaped profile configured to interface closely with one or both of the transverse rods. The rod holder may also have a split aperture to interface with a rod from a spinal instrumentation system. The aperture restriction ring may be applied to secure the split aperture once the rod from the spinal instrumentation system has been introduced into the split aperture. The rod holder may further comprise a female screw thread configured to accommodate a grub screw such that when the rod holder interfaces with the transverse rod and the rod from the spinal instrumentation system, the grub screw can be engaged in the female screw thread in order to secure the hook assembly.

The present invention will now be described, by way of example only, with reference to the accompanying drawings in which.

Various polyaxial locking assemblies are known in the art. The present invention provides for a further alternative improved such assembly.

Figure 9:
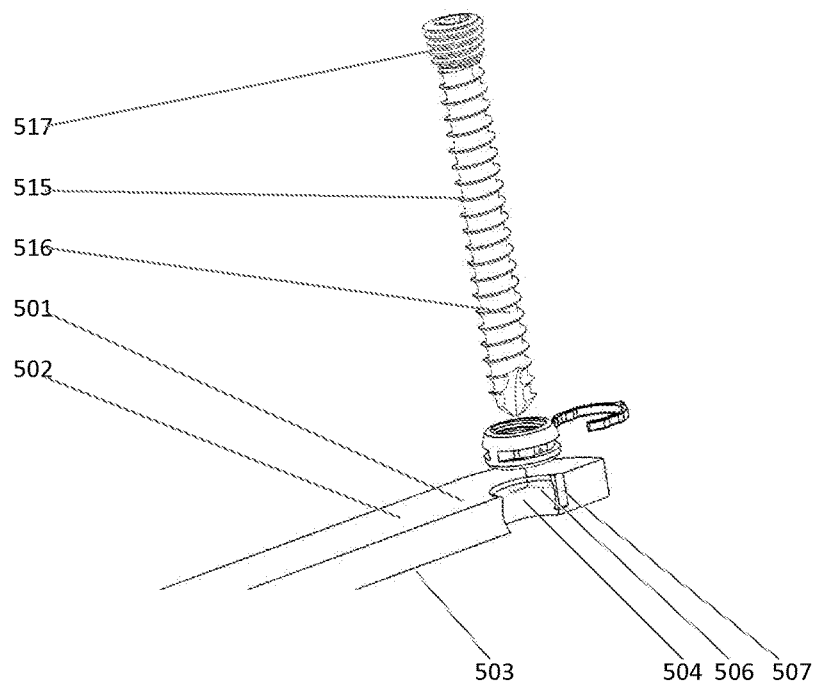
FIG. 9 shows a part perspective of a polyaxial locking system according to a further aspect of the invention.
Figure 10:
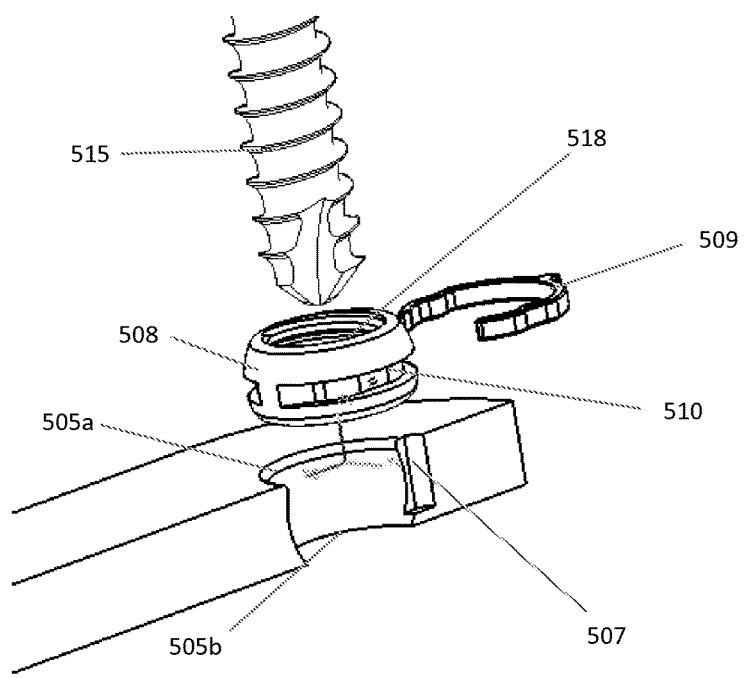
FIG. 10 is a close up of FIG. 9.
Figure 11:
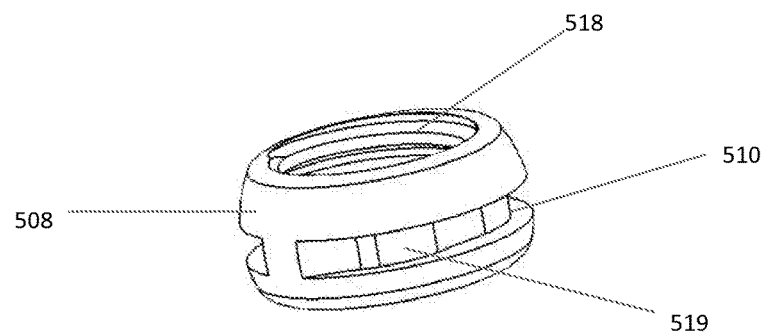
FIG. 11 shows the details of the bushing used in the polyaxial locking assembly of FIG. 9.

FIGS. 9 and 10 show the elements of an alternative polyaxial locking assembly in accordance with the present invention. The embodiment shown includes a receiving member consisting of a plate 501, having a cavity 504 consisting of a spherical through hole to accommodate the other components (508, 509, 515) of the polyaxial locking assembly. In this case the plate has a superior or upper surface 502 and an inferior or lower surface 503. It can be seen in this embodiment that the cavity has a generally spherical inner surface 506 that is truncated top 505a and bottom 505b where the cavity communicates with the upper and lower surfaces of the plate. The plate is also provided with a keyway 507, in this embodiment a blind keyway, which protrudes radially from and communicates with the generally spherical inner surface of the cavity. The keyway originates at the upper surface of the plate but does not exit, in this embodiment, through the lower surface of the plate.

Figure 16:
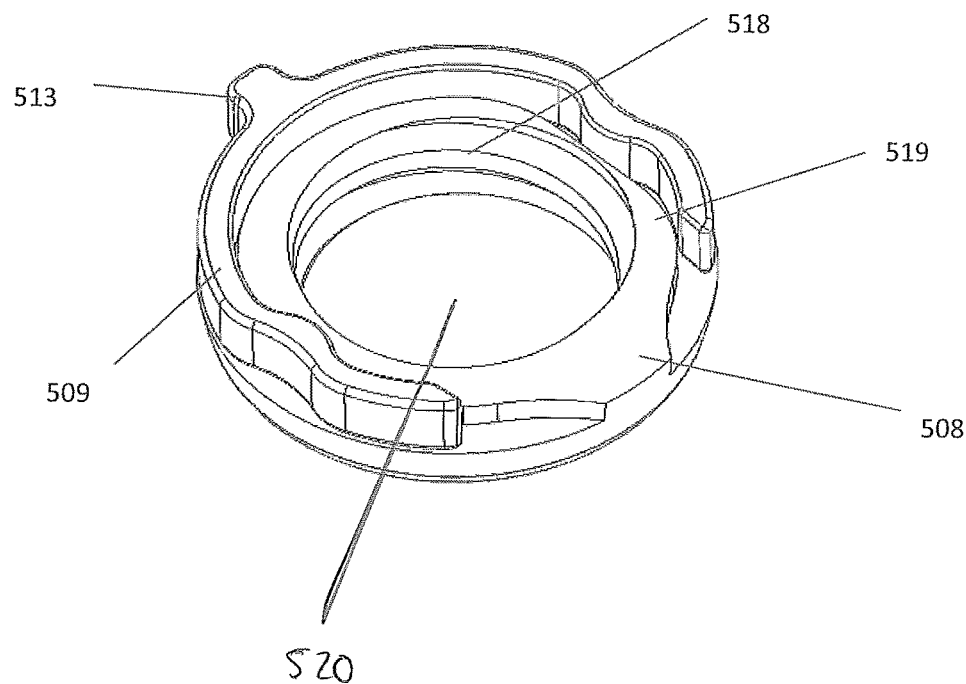
FIG. 16 is a perspective view of the anti-rotation member of FIG. 12 engaged with a section of the bushing of FIG. 11 (the rest of the bushing has been removed for clarity)
Figure 17:
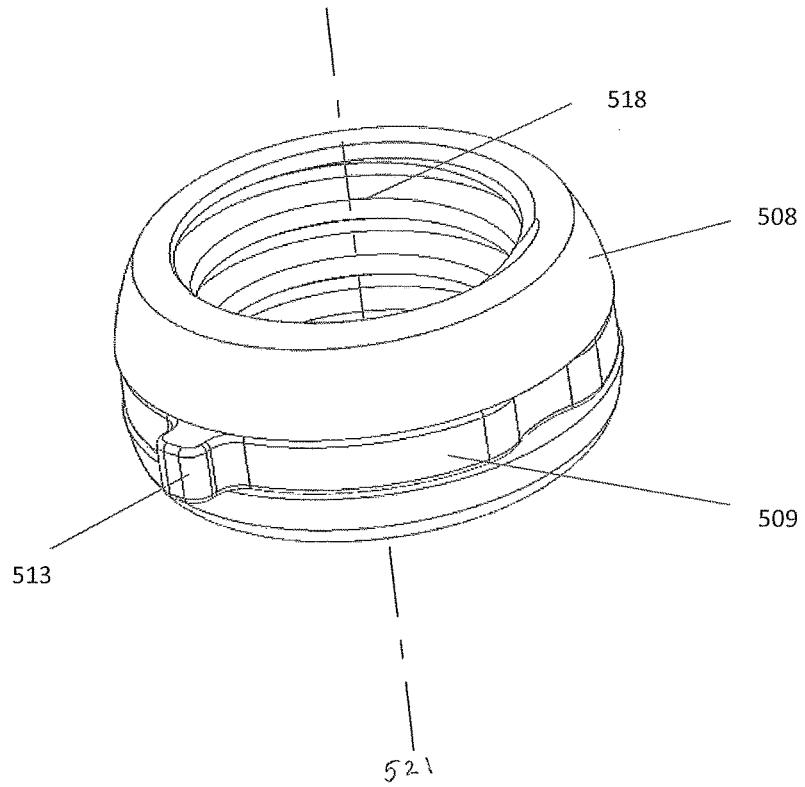
FIG. 17 is a perspective view of the anti-rotation member of FIG. 12 engaged with the bushing of FIG. 11 in its entirety.

The cavity is designed to accept an assembly (FIGS. 15, 16, 17) comprising a bushing 508 and an anti-rotation member 509. In this embodiment the bushing is generally spherical, truncated top and bottom, with an outside diameter to match the generally spherical inner surface of the cavity. Preferentially the parts provide for an initially free movement of the bushing within the cavity. The bushing shown has a hole 520 along its centreline 521, with an internal thread 518 for receiving the locking thread portion 517 of a locking screw 515. In this embodiment the locking screw is for use in attaching the plate to a substrate, in this case a section of bone, and is provided with two distinct threaded regions: a substrate/bone engagement region 516 and a locking thread region 517. In the embodiment shown, the locking thread region is tapered so as to engage with increasing friction within the bushing as it is rotated and screwed in—in alternative embodiments, the locking thread region may be untapered and may have a shoulder at its lower end for engaging with a mating surface within the bushing or may have a head at its upper end which engages with the upper surface of the bushing. The purpose of the taper, shoulder or head is to provide a limit of travel of the screw relative to the bushing, at which point rotation of the screw will of necessity result in a turning motion of the bushing. This is necessary to activate the locking mechanism of the polyaxial assembly.

Figure 12:
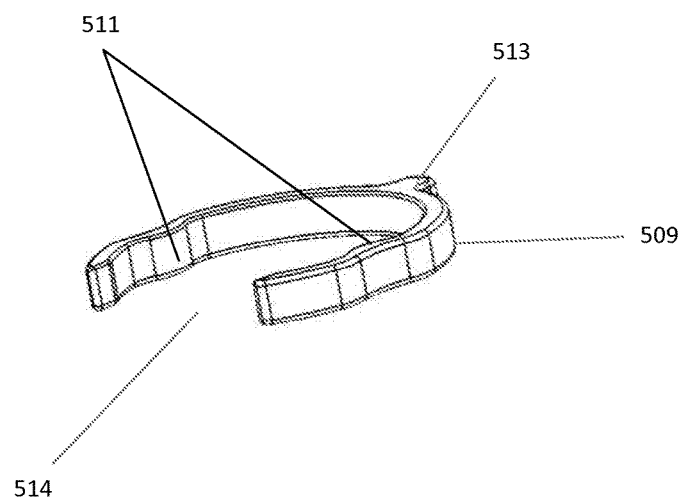
FIG. 12 shows details of the anti-rotation member used in the polyaxial locking assembly of FIG. 9.
Figure 13:
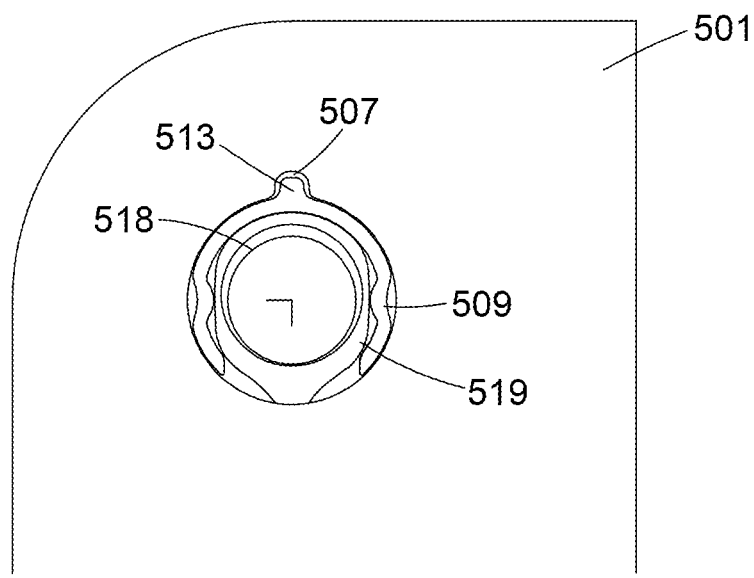
FIG. 13 shows a plan view of the superior surface of the polyaxial locking system shown in FIG. 9, without the presence of a screw.
Figure 15:
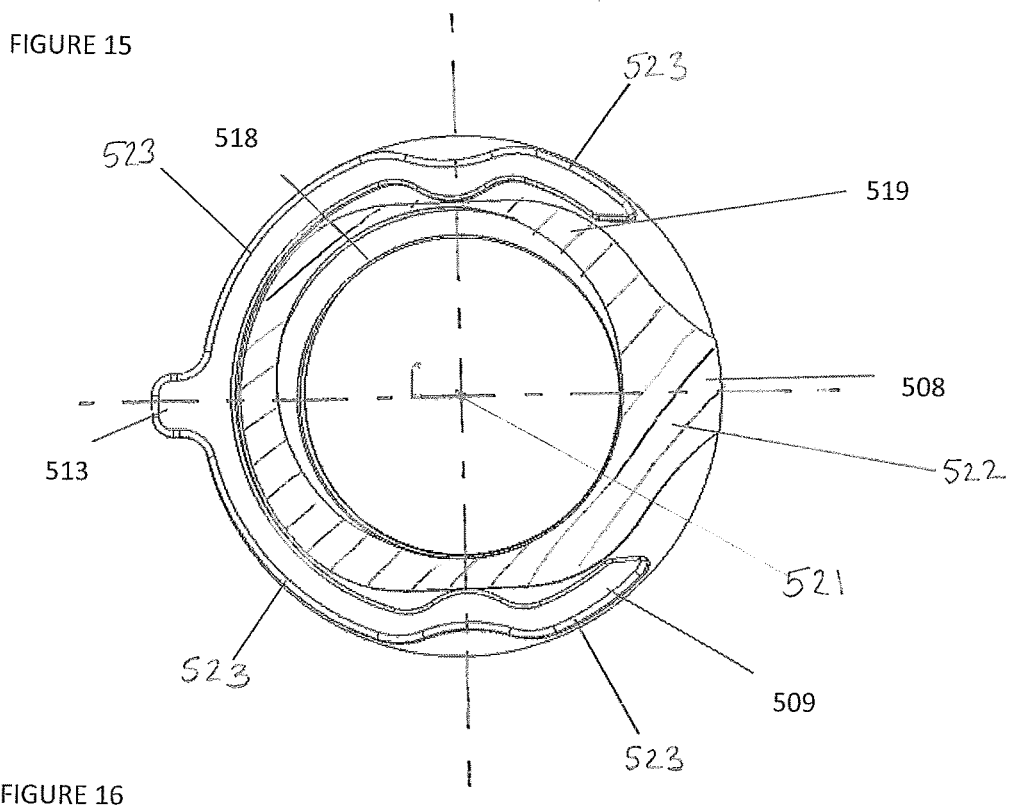
FIG. 15 shows a plan view of the anti-rotation member of FIG. 12 engaged with a section of the bushing of FIG. 11 (the rest of the bushing has been removed for clarity)
Figure 19:
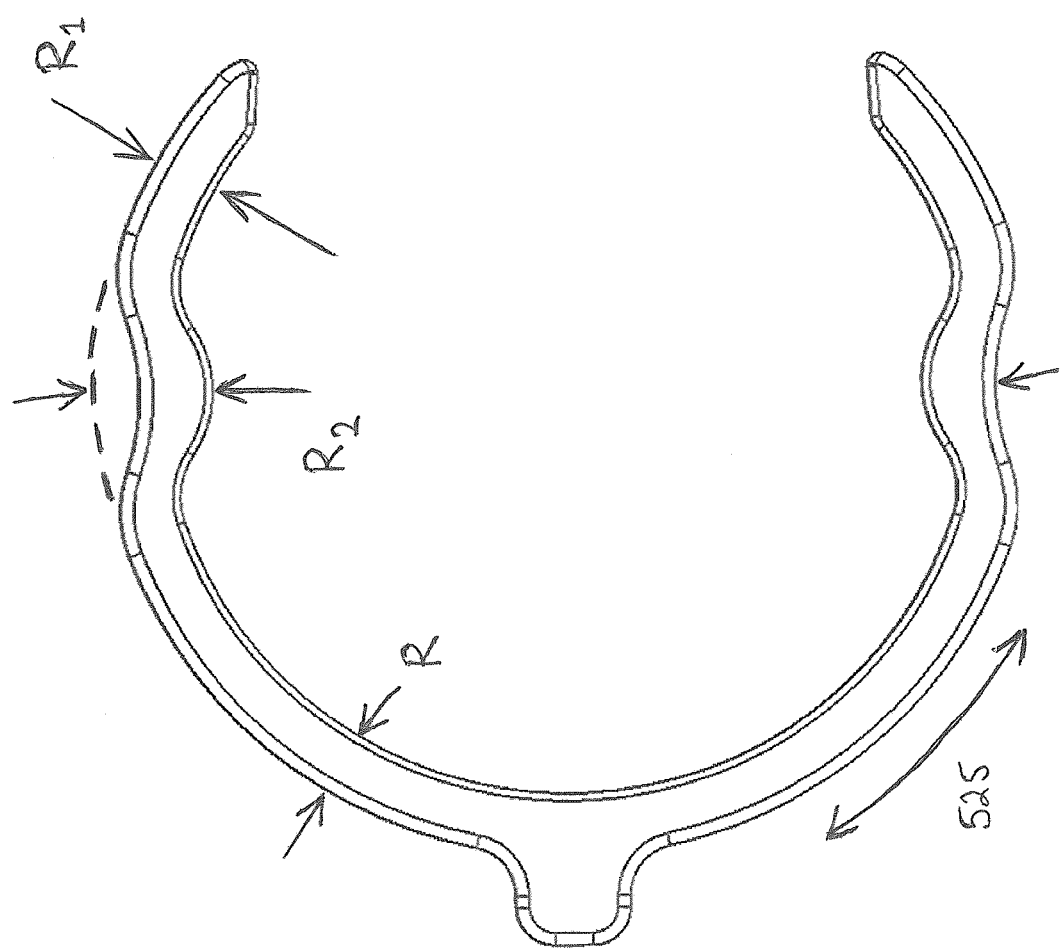
FIG. 19 shows a plan view of the anti-rotation member of FIG. 12.

The bushing (FIGS. 11, 15, 16, 17) is also provided with a groove 510 around its circumference for cooperation with an anti-rotation member (FIGS. 12a, 19). In this embodiment the groove does not encompass the entirety of the circumference, and the anti-rotation member is generally in the form of a c-clip or circlip, i.e.; not a full annular or closed circle device, having a gap 514. This preferential embodiment enables the anti-rotation member to be simply pushed into the groove of the bushing by the application of lateral force. The groove of the bushing is formed such that in cross-section (FIG. 15) it can be seen that the cross-section of the bushing in the plane of the groove (522 hatching) is in the form of a cam, with lobe portions 519 of greater radius than non-lobe portions. As shown in FIGS. 13 and 15, the anti-rotation member is shaped and sized so that initially, it cooperates with the groove such that its outer edge 523 (except for its location key 513) falls within the periphery of the general outer surface of the bushing. The anti-rotation member is also shown provided with a location key 513 which engages in the keyway of the plate when the parts are assembled.

As shown in FIG. 19, the anti-rotation member has a general radial thickness (R). In accordance with the invention, this radial thickness R varies around the circumference of the anti-rotation member. At least one point of the member has a lesser thickness R1 and at least one point of the member has an at least effective greater thickness R2. The greater thickness may be embodied by a simple increased thickness of material at that point, or preferentially as shown in the FIG. 19, the effective or apparent thickness may be embodied by a contour of the anti-rotation member at that point. In the preferred embodiment shown, the anti-rotation member is formed with indents 511 at two points to create an effective greater thickness at those points. Effectively, the anti-rotation member is provided, in the embodiment shown, with radial contouring that provides a pair of leaf springs which create the effective greater thickness R2 of the member at the two points on its circumference. It will be apparent to those skilled in the art that other arrangements could be made to increase the effective thickness of the anti-rotation member, and that instead of two thicker sections, a single thicker section could be provided, or multiples other than two.

When assembled, the anti-rotation member is engaged within the groove of the bushing. The bushing/anti-rotation member assembly is installed in the cavity of the plate, with the location key of the anti-rotation member engaged within the keyway of the plate (FIG. 13). This ensures that the anti-rotation member cannot rotate in the direction of its circumference (525). The bushing and anti-rotation member assembly does, however, retain freedom of movement in the planes perpendicular to the plane of the plate, such that the axis of the bushing (in line with the centreline 520 of the threaded hole 521 for engagement with the screw) is not fixed—this being well known to those skilled in the art as the essence of a polyaxial assembly.

Figure 14:
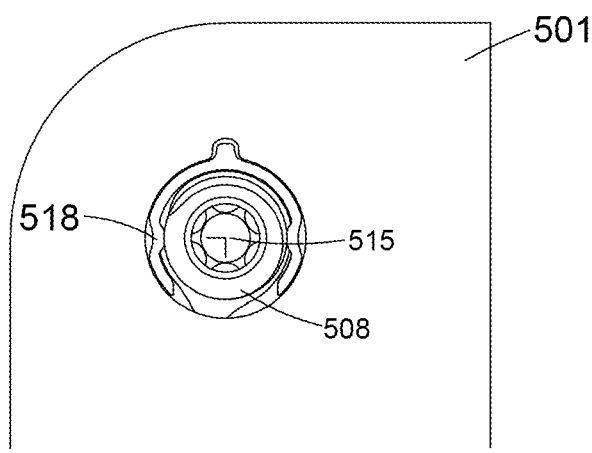
FIG. 14 shows a plan view of the superior surface of the polyaxial locking system shown in FIG. 9, with the screw inserted.
Figure 18:
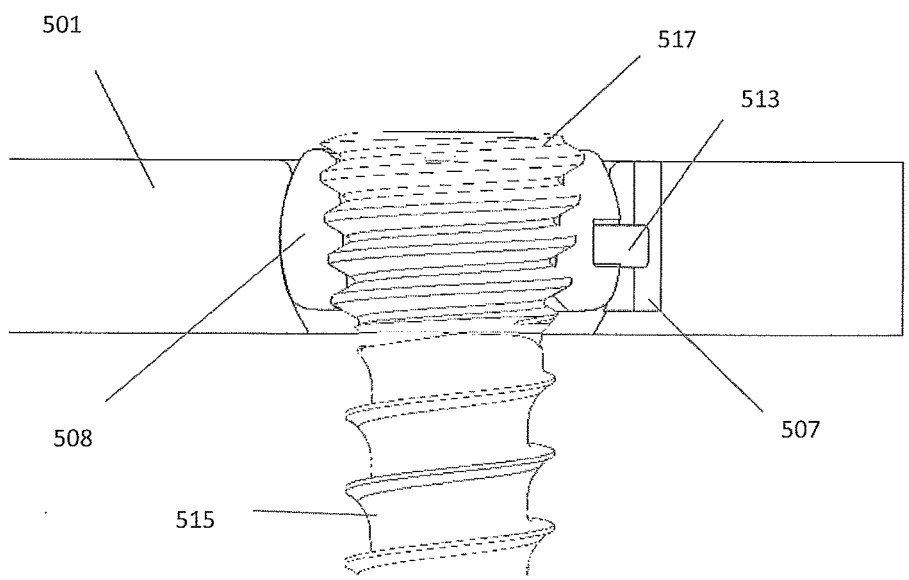
FIG. 18 shows a cross section of the polyaxial locking assembly shown in FIG. 9 with the screw threads engaging with the threads on the inside of the bushing.

Upon insertion of the locking screw, the initial threaded portion passes through the bushing from the upper side of the plate to the lower side of the plate and into the substrate in question—in a preferred embodiment such substrate being bone and the initial threaded portion 516 being a self-drilling, self-tapping and reverse cutting mechanism for insertion into said bone (FIG. 18). The (male) tapered locking thread then begins to engage with the (female) internal thread of the bushing. As the thread advances, the friction begins to rotate the bushing within the cavity. The anti-rotation member is unable to turn with the bushing due to the engagement of the location key with the keyway of the plate. Accordingly, the lobes of the cam cross-section within the groove begin to impinge upon the indented leaf-spring sections 511 of the anti-rotation member, forcing the anti-rotation member to expand so that its outer edge expands beyond the periphery of the generally spherical surface of the bushing (FIG. 14). This creates friction between the components and the cavity inner wall, ultimately resulting in an interference frictional fit of the components and locking the assembly in a desired axial alignment.

In an alternative embodiment, the bushing may be provided with no threading in the hole, the hole having a tapered configuration, and a screw may be provided with a tapered section for cooperation with this tapered hole in the bushing. Provided a force is applied in the axial direction which drives the tapered section of the screw into the tapered section of the bushing, rotation of the screw will result in rotation of the bushing and the locking mechanism of the polyaxial assembly will activate. Such a force may for example be applied in the instance that the screw has a lower section 516 which is screwed into a substrate, resulting in a force which 'pulls' the upper tapered section of the screw into the tapered hole of the bushing. In such an embodiment, one or both surfaces of such unthreaded tapers—female tapered hole in bushing and male tapered section of screw—may be non-smooth so as to increase the amount of available friction. In yet further alternatives, a screw with an unthreaded section and a shoulder may engage with a mating surface in the bushing, or a screw with a head at its upper end may engage with the upper surface of the bushing.

The person skilled in the art will recognise these simply as various methods of providing a means of transmitting torque from a screw to the bushing so as to rotate the bushing and activate the locking mechanism, and will also recognise that other means may be provided for this and that the screw may be replaced with a bolt or other item. In one further alternative, it would be possible to provide the bushing on its upper surface with a slot or slots for a flat-bladed or 'phillips' cross-bladed screwdriver. With the bushing/anti-rotation member assembly in position within the cavity of the receiving member, the bushing could then be rotated by means of a screwdriver until the cam of the groove cross-section engages with the anti-rotation member, so that the bushing/anti-rotation member 'locks' in place in desired orientation. Any screw or bolt or other item may then be attached to the bushing or driven through it with its axis in a particular desired orientation as then defined by the locked-in position of the bushing.

The polyaxial assembly described above, comprising at least a bushing and anti-rotation member, cooperating with a generally spherical cavity with a keyway and optionally also including a screw, may be used in conjunction with the plating system for the anterior pelvic ring as described below; the polyaxial assembly being used in place of the locking mechanism also described below. It will of course be readily understood by those skilled in the art that the polyaxial assembly described may be used in any number of applications, indeed any application where a polyaxial screw with a locking mechanism is required. In particular, the assembly may be used in any of the applications typical in the field of orthopedics, where various types of plate or support systems require affixing to skeletal structures of the human or animal corpus.

Figure 1:
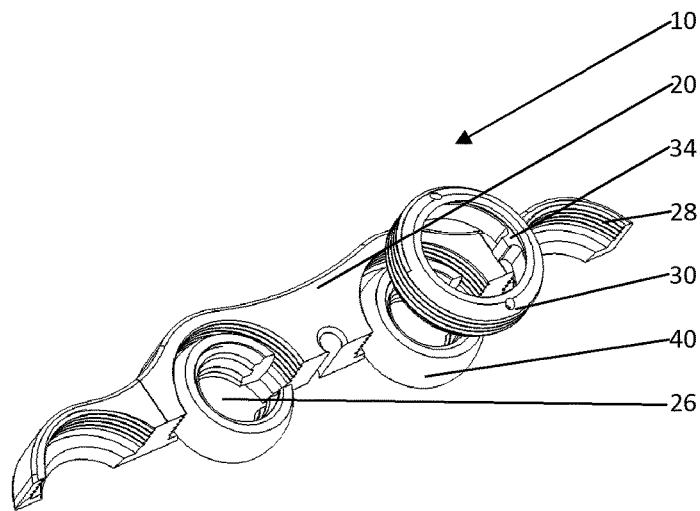
FIG. 1 shows a part-perspective view of a locking mechanism according to one aspect of the present invention.
Figure 2:
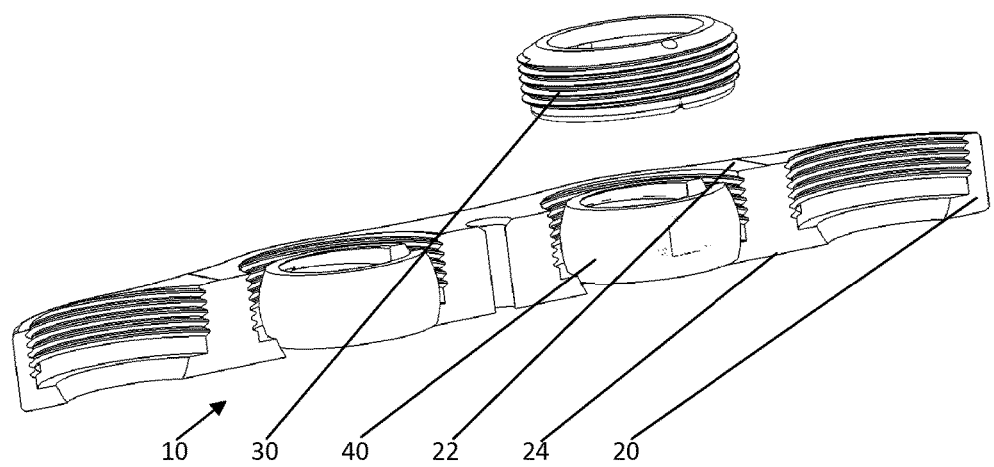
FIG. 2 shows a cross section through the locking mechanism of FIG. 1.

FIGS. 1 and 2 show a locking mechanism 10 according to a further aspect of the present invention. The locking mechanism includes a plate 20, a bushing 30 and a split grommet 40. The plate 20 comprises upper and lower surfaces 22, 24 and an opening 26 that extends through the plate 20 from the upper surface 22 to the lower surface 24. The opening 26 has a part-spherical geometry which is provided with a screw-thread 28. The lower surface 24 of the plate 20 is scalloped to provide for adequate clearance of the grommet 40 from the bone surface at maximal angulation. This feature also provides for a low contact area between the plate 20 and the bone, thus optimising the periosteal blood supply. The scalloping increases the cross-sectional diameter of the plate from the minimal functional cross-sectional diameter of approximately 5 mm required for fatigue tolerance.

The bushing 30 is annular and comprises an inner surface that has is part-spherical in cross section. On the outer surface is provided with a screw-thread 32. The bushing 30 is sized such that the screw-thread 32 on the outer surface can interface with the screw-thread 28 lining the opening 26 in the plate 20. The bushing 30 is also provided with a tab 34 that protrudes radially inwardly from the part-spherical inner surface of the bushing 30.

The split grommet 40 has an outer surface 42 that has a part-spherical profile and an inner surface that is provided with a screw-thread 44 for engagement, in use, with a locking screw. The split grommet 40 is capable of rotation in the X- and Y-axes (as illustrated in FIGS. 1 and 2) relative to the plate 20 and the bushing 30. This rotation enables the screw-thread 44 for engagement, in use, with the screw to rotate relative to the plane of the plate 20 by up to 30° either side of the neutral position, therefore providing a total polyaxial arc of 60°. The tab 34 that projects from the bushing 30 constrains rotation of the grommet 40 around the Z axis to an arc of approximately 8°. This arc and implicitly the ratio of the tab dimensions to those of the split in the grommet allow for free rotation of the grommet around the non-constrained axes, within and up to the design limit wherein the arc subtended is approximately 15° to either side. The screw-thread 44 on the inner section of the grommet is a tapered, square-section female thread of approximately 17° taper angle. The angle of taper of the thread must be sufficient to push the grommet 40 outwards to form an interference fit with the bushing 30. However, if the taper angle is too great then the torque provided to apply the screw becomes prohibitively high. Therefore, whilst 17° taper is preferred, the taper may be selected between 3° and 20°.

Figure 3:
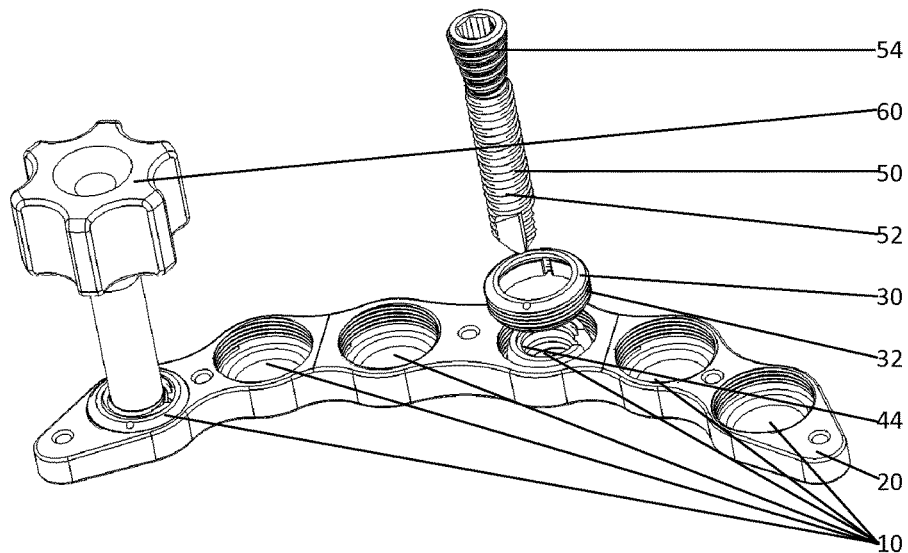
FIG. 3 shows the locking mechanism of FIG. 1 in the context of a plating system for the anterior pelvic ring.

One example of a locking insertable screw 50 for use with the locking mechanism 10 is shown in FIG. 3. There are two distinct threaded regions provided: a bone engagement thread 52 and a locking thread 54. There may be a non-threaded section between the two threaded regions. The bone engagement thread 52 is a self drilling, self-tapping and reverse cutting mechanism. It is also a cortical screw thread which provides a larger core diameter than a cancellous screw. The locking mechanism engagement thread 54 is resistant to cross-threading and is preferably a male square-section thread of approximately 17° taper angle which engages the screw-thread 44 for engagement which is preferably a female square-section thread. Although 17° is exemplified here, the taper of the bone engagement thread 52 must be the same as that of the locking thread 54. If there is a difference in pitch between the bone engagement thread 52 and the locking thread 54, this may result in compression. As a result, the plate may move away from the bone or, conversely, the contact with the bone may be complete before the grommet 40 is locked. The two threaded regions are configured to ensure that there is no contact between the bone engagement thread 52 and either the grommet 40 or the plate 20 within the design limits of the polyaxial arc provided by the rotation of the grommet 40 within the opening in the plate 20.

The provision of the part-spherical surfaces on the inner surfaces of the opening in the plate 20 and the bushing 30 and the outer surface of the grommet 40 ensure that there is a high contact area between the components.

The use of square section threads provides a resistance to cross-threading and the capacity of the thread to cause radial expansion of the grommet as the taper of the locking screw 50 engages.

The finish of the contact area between the plate 20, the bushing 30 and the grommet 40 is profiled in such a way as to facilitate a high level of friction between the assembled components and thus a friction interference fit during the process of radial expansion. The tolerances of the component parts prior to engagement of the locking mechanism are such that low friction rotation of the grommet within the design arc is possible.

Alignment of the locking mechanism with the drilled hole in bone is facilitated by means of a drill guide 60 which is provided with a male thread 62 at its distal end that engages the female tapered square-section locking thread of the grommet 40. The diameter of the drill is smaller than that of the core diameter of the cortical screw such that insertion of the screw causes radial expansion and impaction of the surrounding bone which improves pull-out resistance in cancellous bone.

The plate 20, bushing 30 and grommet 40 are fabricated from titanium alloys, in particular, titanium alloys that include aluminium and vanadium. They may also be surface finished to improve the fatigue strength of the parts. In addition, the surface finishing may include electroplating enabling the parts to be colour coded to aid quick identification of the parts.

FIG. 3 shows a plate 20 that is configured for use as a symphyseal plate. Such a plate 20 is indicated for specific fracture-dislocation patterns of the anterior pelvic ring which include symphyseal diastasis and juxta-symphyseal fractures of the superior and inferior pubic rami associated with vertically stable, Tile Type B injuries of the posterior pelvic ring and symphyseal pseudo-diastasis. Fractures extending lateral to the medial border of the obturator foramen require supplemental anterior ring stabilisation with, for example cannulated anterior column screws or an external fixator device. It is recommended that symphyseal plate stabilisation of the anterior pelvic ring is supplemented by posterior ring stabilisation in the case of vertically unstable Tile Type C injuries.

The symphyseal plate 20 is arcuate and is contoured to match the radius of the pelvic inlet at the symphysis pubis, extending into the superior pubic ramus. The maximal depth of the plate 20 is of the order of 5 mm which is similar to the dimensions of plates designed to resist fatigue failure in long bone fractures. Each end 29 of the plate 20 beyond the most laterally distant of the openings 26 is tapered in two planes to facilitate ease of passage under the soft tissues required of minimally invasive surgical approaches. The plate 20 is also wasted around each of the openings 26.

The plate contains cylindrical bores to accommodate 2 mm K-wires which may be utilised for the temporary positioning and stabilisation of the plate and prior to insertion of the poly-axial locking screws.

Although the example illustrated in FIG. 3 has six locking mechanisms 10, other examples may be provided with four locking mechanisms 10. In the example with four locking mechanisms, these four locking mechanisms provide for the optimal length and orientation of the locking screws in the juxta-symphyseal anatomy which are divergent in the case of the most medial screws and convergent in the case of the next most lateral pair. In the illustrated example, the additional two locking mechanisms, one at each end of the plate 20 may be orientated to optimal advantage according to the configuration of the fracture. The combination of convergent and divergent screw orientation provides for the optimal stability and pull out strength consistent with locking plate theory and the applied anatomy.

In addition to the four- and six-locking mechanism configurations, other applications may provide for a plate with a greater number of locking mechanisms in a range of different configurations. Other applications may provide for a plate constructed of materials other than a titanium alloy in order to provide a closer matching of the modulus of elasticity for that of cancellous bone. Such materials may include carbon fibre reinforced poly-ethyl-ethyl-ketone (PEEK).

Figure 4:
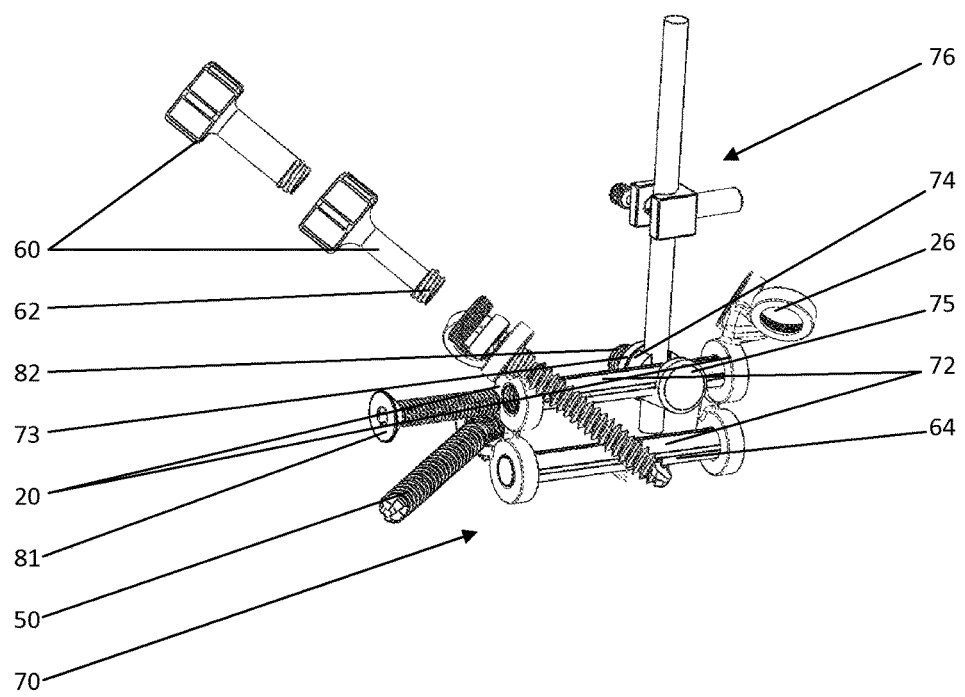
FIGS. 4 and 5 show the locking mechanism of FIG. 1 in the context of a plating system for the posterior pelvic ring.
Figure 5:
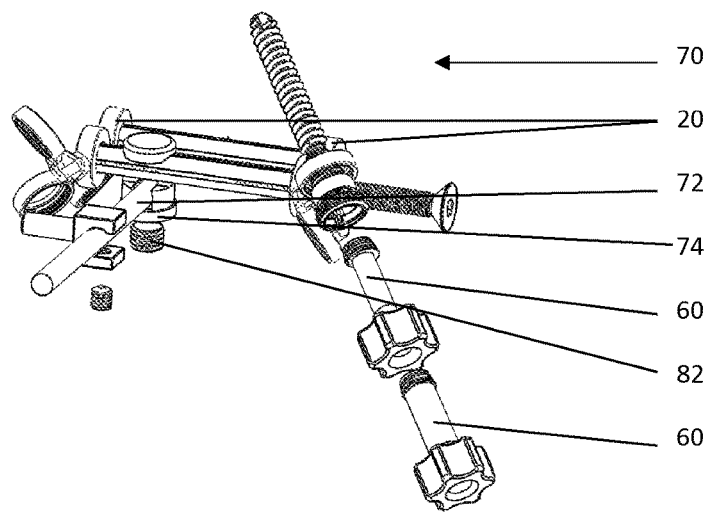

An example of a posterior pelvic reconstruction system 70 is illustrated in FIGS. 4 and 5. The system 70 comprises two mirror-image plates 20; two transverse rods 72; a plurality of locking screws 50; and a hook assembly 74 for attaching a spinal instrumentation system 76 to either one, or both, of the transverse rods 72. Attachment to both of the transverse rods 72 provides optimal torsional stability. The hook assembly 74 is provided only when a spinal instrumentation system 76 is required. In some circumstances a spinal instrumentation system may not be required and, in such instances, the hook assembly 74 would not be included in the posterior pelvic reconstruction system 70.

The locking screws 50 may be cortical or cancellous. However, as the diameter of the core is increased, the resistance to fatigue failure also increases. Therefore, cortical screws may be used in preference over cancellous screws. Indeed, the screws used may have a larger than standard core diameter.

The posterior pelvic reconstruction system 70 provides for a biomechanically optimised device which is specific to the complex anatomical configuration of the posterior pelvic ring and takes account of the fact that the sacrum is a transitional zone between the pelvic ring and the axial skeleton or spine. Fracture-dislocations of the posterior pelvic ring are subject to complex, cyclical loading patterns with six degrees of freedom in single leg stance and may be inclusive of or independent of axial skeletal stability. "H"-pattern fractures for example require extension of the internal reconstruction configuration into the L5 and L4 pedicles. Furthermore and by inference, stability of the axial skeleton or spine in the case of long segment spinal fusions which include the lumbar-sacral junction require stable fixation into the pelvic ring.

The plates 20 are anatomically contoured to be applied to the medial surface of the posterior iliac crests which requires that the plates are right and left sided, i.e. the two plates 20 are substantially mirror images of one another. The plates 20 provide a stable platform for the internal fixation of adjacent anatomical structures which include the greater sciatic buttress of the right and left hemi-pelvis and the S1 pedicles. In order to achieve this fixation, each of the plates is provided with a plurality of locking mechanisms 10 which provide poly-axial fixation by virtue of the angular deviation between the fenestrations or openings 26 in the plates 20 and also by virtue of the three component locking mechanism 10 described above with reference to FIGS. 1 and 2.

A female threaded section may provided at either end of the cannulated section for engagement with a right hand threaded compression bolt 81. Two compression bolts are provided of which only one is shown. The compression bolts configured to be passed, in use, through drill holes in the posterior iliac crests. As the bolts 81 are tightened, the tapered section engages the countersunk outer cortex of the iliac crest, providing compression between the iliac crest and the transverse rod 72 and thus resisting disengagement of the transverse rod 72 from the plates 20.

One of the transverse rods 72, typically the uppermost rod, that links the left and right plates 20 may be cannulated. The transverse rods 72 are provided with textured longitudinal slots 64 which engage male threaded grub screws. These screws engage female threaded fenestrations 26 in the plate 20. This arrangement has a dual function. The friction fit of the grub screws with the textured surface of the slot 64 prevents disengagement of the transverse rods 72 from the plates 20. Furthermore, the grub screws, by engagement with the plates 20 and the slots 64 prevent rotational distortion of the trapezoid formed by the transverse rods 72 and the plates 20. The transverse rods 72 together with the left and right plates 20 provide a stable link between instrumentation of the right and left hemi-pelvis and thus completing the posterior pelvic ring. The trapezoidal shape created between the two plates 20 and the two rods 72 ensures this stability within the system.

Further vertical stability may be gained in both pelvic and spinal instrumentation applications by means of extension into the L5 and L4 pedicles or beyond. This process requires hybridisation with generic spinal instrumentation systems and is facilitated by the hook assembly 74 applied to the transverse rod 72. The hook assembly 74 operates as a compression system comprising a rod holder 75; a grub screw 82 and an aperture restriction ring 73. The rod holder 75 has a C-shaped cross section hook sized to conform to the transverse rod and a split aperture that has a smooth interior surface that is sized to conform to a rod 68 that forms part of the spinal instrumentation system 76. In one of the extremities of the C-shape (at the top of the holder 75 as illustrated) there is provided an indented female thread into which the grub screw 82 may be introduced. The grub screw is typically an M8 grub screw, although other sizes may be used as appropriate. Initially, the rod holder 75 engages the transverse rod 72. The rod 68 from the spinal instrumentation system 76 can then be introduced into the split aperture. The split aperture is then secured by the aperture restriction ring 73. As a result of the configuration of the rod holder 75 the rod from the spinal instrumentation system 76 and the transverse rod 72 are engaged in a substantially orthogonal configuration. The grub screw 82 is introduced into the female thread the interior surface of the C-shape forms an interference fit with the transverse rod 72 thus holding the rod holder 75 in place.

But for the novel configuration described above with reference to FIGS. 4 and 5, on contact with the spinal instrumentation rod, a grub screw would typically engage both the rod and the cross-member by mutual compression but at the same time would cause radial expansion of the split aperture and therefore failure of the lock. In conventional spinal instrumentation systems, this process is resisted by either a threaded outer aperture ring nut or by increasing the cross-sectional area of the split aperture. In the case of the former solution, the technique requires sequential and incremental application of the grub screw and the threaded outer aperture ring nut which is prone to cross-threading and requires torque limitation. In the case of the latter solution, the device is bulky which is not well suited to the anatomical constraints in this application.

The hook assembly 74 described above with reference to FIGS. 4 and 5 allows for a low profile device of minimal cross-sectional area, consistent with the applied loads. It is applied prior to the grub screw 71 and is not therefore prone to sequential cross-threading or friction lock. The interfacing surfaces are prepared so that the hook assembly 74 will slip on easily and, as the ring 73 resists radial expansion of the split aperture, the assembly 74 is effectively held in place by a friction interference fit.

In this manner, the hook assembly 74 links the proximal and, if necessary, the distal transverse rods 72 to a vertically disposed 5.5 mm spinal instrumentation rod 68 which forms part of the spinal instrumentation system. Whilst the example illustrated in FIGS. 4 and 5 utilises a 5.5 mm rod 68, rods of different diameters, including for example 6.0 mm and 6.5 mm may also be used. The larger diameter rods are especially suited to situations where there is considerable instability of the pelvis. The rod 68 may be easily contoured to mono-axial or poly-axial pedicle screws, pedicle hooks, lamina hooks and sub-laminar wires as required from the level of L4 and proximally. As the L5 pedicle is laterally disposed with respect to the L4 pedicle, it is not well suited in this application to incorporation with an extended spinal instrumentation rod assembly which would require excessive contouring of the rod. In order to address this, a link device 85 is provided at the L5 level. The link device 85 comprises a C-shaped cross section clamp to conform to the spinal instrumentation rod 68 and a 5.5 mm rod of cylindrical section which engages the L5 pedicle screw. The C-shaped cross section clamp is secured to the spinal instrumentation rod 68 with a grub screw 71 and the link device 85 thus links the L5 pedicle screw and the spinal instrumentation rod with the appropriate offset.

The system 70 allows for the internal fixation of most dissociations of the pelvic ring and those of the pelvis and axial skeleton. The biomechanics of spinal-pelvic stabilisation requires that the instrumentation extends anterior to the "pivot point" which is defined as the osteo-ligamentous column at the level of the L5-S1 junction and corresponds to the coronal plane of the posterior longitudinal ligament.

Figure 6:
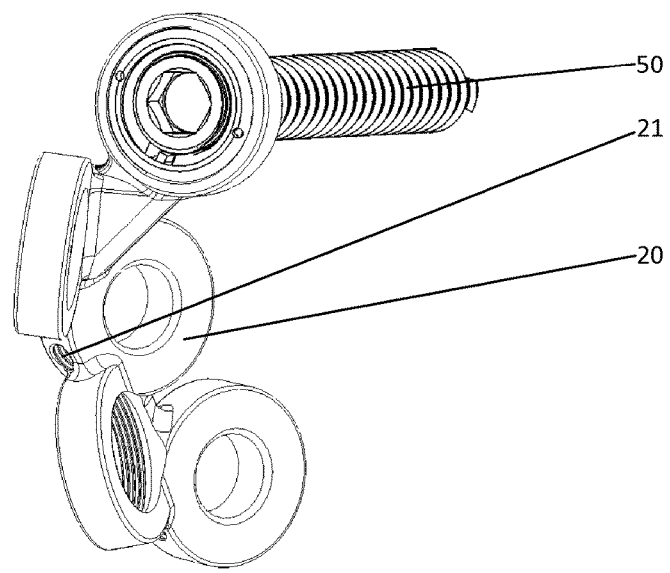
FIG. 6 shows the detail of a locking plate used in the plating system of FIGS. 4 and 5.

FIG. 6 shows more detail relating to the locking plates 20 used in the system 70. The anatomically contoured poly-axial locking plates 20 have a unique and anatomically matched geometry, effectively linking two cortical profile, self-drilling, self-tapping poly-axial locking screws 50 which are positioned as inter-table screws in the greater sciatic buttress and a further cancellous profile self-drilling, self-tapping S1 pedicle screw 56 which protrudes at an angular deviation of approximately 60°. The exact angular deviation between the cortical 50 and cancellous 56 screws will be determined by the anatomy. All three screws 50, 56 extend anterior to the pivot point and the configuration bridges, but does not transgress the sacro-iliac joint. The inter-table screws 50 are applied by drilling at a smaller diameter than the core diameter of the screw 50. In this way, as the screw 50 is introduced, it will result in the radial expansion of the cancellous bone.

Fracture-dislocations of the posterior pelvic ring are in general associated with fracture-dislocations of the anterior pelvic ring, thus the symphyseal plating system described with reference to FIG. 3 may be used in conjunction with the posterior pelvic reconstruction system described with reference to FIGS. 4 and 5. The symphyseal plating system offers supplementary anterior ring stabilisation for the indications described above. The configuration of the system is optimised to resist vertical displacement forces, lateral translation forces and rotational forces in the saggital plane. Adequate stabilisation of the anterior pelvic ring should resist external rotation forces and tensile loads in the cross-members are resisted by the superior cross-member sink compression screw.

Fractures of the pelvic ring comprising a diastasis of the symphysis pubis in association with fractures of either all or some of the pubic rami provide for a difficult clinical problem in respect of the choice of internal fixation with conventional devices. Typically, the symphyseal diastasis may be stabilised by means of a symphyseal plate and screws. Fractures of the pubic rami may be stabilised by means of anterior column screws. In the case of a fracture dislocation combining these patterns, the trajectories for the screws of one device are obstructed by those of the other. The commonly employed alternative of a symphyseal plate in combination with an external fixator device lacks biomechanical strength and there is an inherent risk of pin track infections from the external fixator device. A further procedure is then required to remove the external fixator device.

Figure 7:
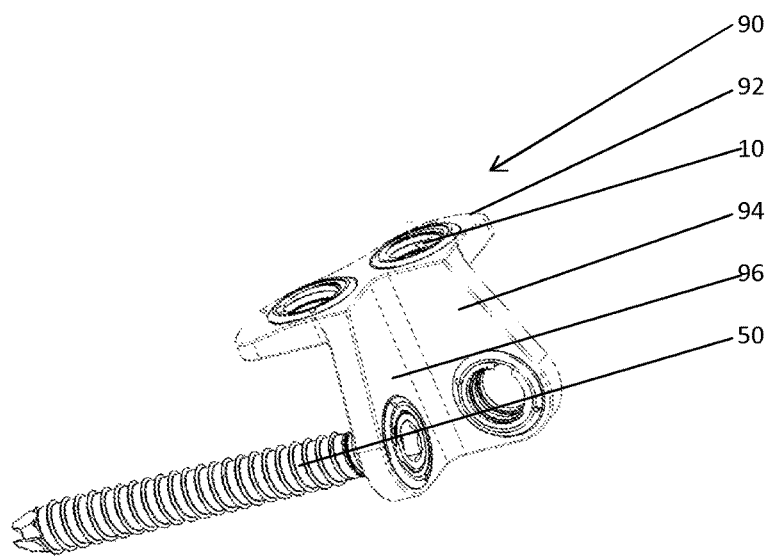
FIG. 7 shows the symphyseal wedge plate which is indicated for a combination of symphyseal diastasis and fractures of the pubic rami.

FIG. 7 illustrates the symphyseal wedge plate 90 which is indicated for this combination of injuries. The wedge plate 90 is configured to provide for stable internal fixation by combining the techniques of symphyseal plating and anterior column screws in a single application. The wedge plate 90 comprises three plates: a superior plate 92 and two vertical plates 94, 96. The three plates 92, 94, 96 are disposed orthogonally. The superior plate 92 accommodates two polyaxial cortical locking screws 50 which may be orientated divergently in the juxta-symphyseal bone stock. The polyaxial locking mechanism 10 is as described above with reference to FIGS. 1 and 2. The vertically disposed plates 94, 96 each accommodate one polyaxial locking screw 50, the centre of which is disposed at 20 mm or thereabouts from the upper surface of the superior plate 92. The lower array of polyaxial locking screws 50 are orientated in an approximately orthogonal orientation to each other and to the locking screws 50 of the superior plate 92. They are designed to align with the entry point for anterior column screws. The polyaxial locking mechanism 10 is similar in design to those of the superior plate 92 but may accommodate cortical, cancellous or cannulated screws including partially threaded cancellous screws as suited to the particular fracture pattern. The polyaxial mechanism 10 is provided with drill or wire guides 60 that engage with the female thread in the bushing 40. Appropriate placement of the symphyseal wedge plate 90 requires the resection of an anteriorly based wedge comprising juxta-symphyseal bone and the proximal 25 mm of the symphyseal fibro-cartilage. The margins of the resection are disposed at 90 degrees to one another and are facilitated by means of a gig. The strength of the construct derives from the relative orientation of the planes with respect to the disposition of the plates and the polyaxial locking screws 50.

Figure 8:
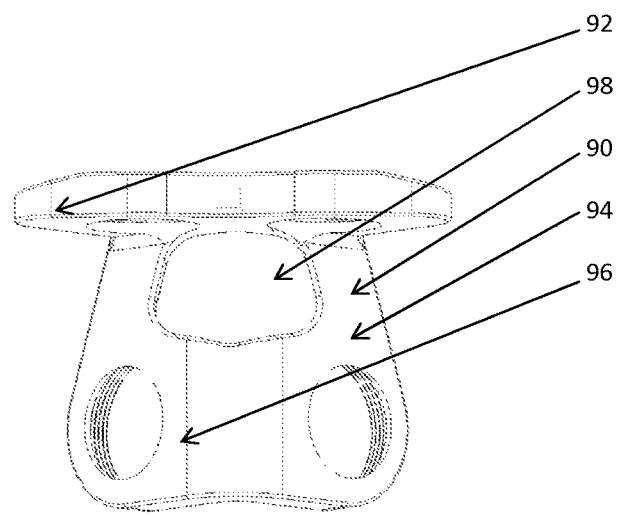
FIG. 8 shows a further symphseal wedge plate including a fenestration.

FIG. 8 illustrates a variation of the symphyseal wedge plate 90 which provides for a fenestration 98 in the construct, orientated between the vertical plates 94, 96 of the wedge plate 90 and thereby allowing for the placement of a cancellous or cortico-cancellous bone graft intended for the purpose of symphyseal fusion. This example extends the indications to a symphyseal fusion which may be of use in post-traumatic or post-partum symphyseal instability.

The invention claimed is:

1. A polyaxial locking assembly comprising:
   a receiving member comprising at least one open cavity having a generally spherical inner surface;
   a bushing with a generally spherical outer surface sized and shaped to fit within the cavity, said bushing comprising a hole aligned with an axis of the bushing, said hole further provided with a female thread;
   a screw provided with a male thread for engagement, in use, with the bushing and the hole and thread thereof;
   wherein the open cavity is provided with at least one radially outwardly protruding keyway; the bushing further comprising a groove aligned with a perimeter of the bushing, said perimeter being on a plane substantially orthogonal to the bushing axis, the bushing groove being shaped so that the bushing, at a perimeter of the groove and on said plane, provides a cam, said cam having at least one lobe; there is further provided an anti-rotation member that, in use, is positioned within the bushing groove between the cam and an inner surface of the cavity, the anti-rotation member further comprising a key for cooperative engagement with the cavity keyway such that the ability of the anti-rotation member to rotate within the cavity is restrained; the anti-rotation member further having a generally annular, open or closed geometry and having a radial thickness, and further being contoured such that at least one portion of the anti-rotation member has an effective radial thickness greater than that of at least one other portion;

such that in use, the screw may be threaded into the bushing until it reaches a limit of travel, whereupon further rotation of the screw also rotates the bushing, forcing the effectively radially thicker portion of the anti-rotation member outwards so that the anti-rotation member engages with the inner surface of the cavity and causes a build up of friction between the cam, the anti-rotation member and the inner surface of the cavity, so as to lock the assembly in a desired orientation.

\* \* \* \* \*